US011208413B2

(12) United States Patent
Hewitt et al.

(10) Patent No.: US 11,208,413 B2
(45) Date of Patent: Dec. 28, 2021

(54) PYRIMIDOPYRIMIDINONES USEFUL AS WEE-1 KINASE INHIBITORS

(71) Applicant: ALMAC DISCOVERY LIMITED, Craigavon (GB)

(72) Inventors: Peter Hewitt, Craigavon (GB); Frank Burkamp, Craigavon (GB); Andrew Wilkinson, Craigavon (GB); Hugues Miel, Craigavon (GB); Colin O'Dowd, Craigavon (GB)

(73) Assignee: ALMAG DISCOVERY LIMITED, Craigavon (GB)

( * ) Notice: Subject to any disclaimer, the term of this patent is extended or adjusted under 35 U.S.C. 154(b) by 0 days.

(21) Appl. No.: 16/492,292

(22) PCT Filed: Mar. 12, 2018

(86) PCT No.: PCT/GB2018/050620
§ 371 (c)(1),
(2) Date: Sep. 9, 2019

(87) PCT Pub. No.: WO2018/162932
PCT Pub. Date: Sep. 13, 2018

(65) Prior Publication Data
US 2021/0128560 A1 May 6, 2021

(30) Foreign Application Priority Data
Mar. 10, 2017 (GB) .................................. 1703881

(51) Int. Cl.
C07D 487/04 (2006.01)
A61P 35/00 (2006.01)
A61K 31/519 (2006.01)

(52) U.S. Cl.
CPC .......... *C07D 487/04* (2013.01); *A61K 31/519* (2013.01); *A61P 35/00* (2018.01)

(58) Field of Classification Search
None
See application file for complete search history.

(56) References Cited

U.S. PATENT DOCUMENTS 7,196,090 B2    3/2007  Connolly et al.
2016/0318936 A1* 11/2016 Harrison ................. A61P 35/00

FOREIGN PATENT DOCUMENTS

WO    WO 2004/011465 A1   2/2004
WO    2015/092431          6/2015

OTHER PUBLICATIONS

DO. Cell Cycle, 2013, 12:19, 3159-3164 (Year: 2013).*
International Search Report and Written Opinion, corresponding to PCT/GB2018/050620, dated Sep. 5, 2018.

* cited by examiner

*Primary Examiner* — Noble E Jarrell
(74) *Attorney, Agent, or Firm* — Lathrop GPM LLP; Brian C. Trinque, Esq.

(57) ABSTRACT

The present invention relates to a compound that is useful as an inhibitor of the activity of Wee-1 kinase. The present invention also relates to pharmaceutical compositions comprising this compound and to methods of using this compound in the treatment of cancer and methods of treating cancer.

12 Claims, No Drawings

PYRIMIDOPYRIMIDINONES USEFUL AS WEE-1 KINASE INHIBITORS

RELATED APPLICATIONS

This application is a 35 U.S.C. § 371 filing of International Application No. PCT/GB2018/050620, filed Mar. 12, 2018, which claims the benefit of Great Britain Patent Application No. 1703881.1 filed Mar. 10, 2017. The entire contents of these applications are incorporated herein by reference in their entireties.

The present invention relates to a compound that is useful as an inhibitor of the activity of Wee-1 kinase. The present invention also relates to pharmaceutical compositions comprising this compound and to methods of using this compound in the treatment of cancer and methods of treating cancer.

BACKGROUND TO THE INVENTION

Cells are continually challenged on a daily basis, resulting in multiple lesions forming in DNA. The lesions, if not repaired, can lead to mutations or cell death, thus complex signalling networks exist which ensure that lesions are detected and repaired to maintain the integrity of DNA.

Detection of DNA damage initiates a series of events which are key in maintaining the genome integrity. Cell cycle checkpoints are designed to stop the cell cycle and allow repair of the lesion before allowing the cell to continue into mitosis.

Two key checkpoints have been identified, one at the end of the G1 phase and the second at G2, working in tandem to ensure all lesions are identified and repaired. In around 50% of human cancers the G1 checkpoint is non-functional due to mutations in the tumour suppressor gene TP53. However, the G2 check-point is seldom mutated and often found to be activated in cancer cells. Cancer cells exploit this to confer resistance to treatment modalities, including DNA damaging agents and radiation.

Three kinases have been identified as key regulators of the G2 checkpoint, namely Chk1, Chk2 and Wee-1. Inhibitors for these kinases are currently being evaluated in clinical trials.

Wee-1 is a nuclear tyrosine kinase which negatively regulates entry into mitosis at the G2/M check-point by catalysing a phosphorylation of the cdc2/cyclin B kinase complex. The phosphorylation occurs on the tyrosine-15 residue and leads to the inactivation of the cdc2/cyclin B complex, ultimately preventing mitosis. Wee-1 function is intimately linked to that of Chk1 and Chk2 due to their phosphorylation and inactivation of cdc25 on serine-216, as well as the reported activation of Wee-1 by Chk 1 & 2 (Ashwell, 2012, *DNA Repair in Cancer Therapy, DOI:* 10.1016/B978-0-12-364999-1.10010-1).

Wee-1 is downstream of the Chk family and is a crucial component of the checkpoint signalling cascade as it prevents cells from entering mitosis if lesions are detected (Do et al., Cell Cycle 2013 12 (19) 3159-3164.

Commonly administered anti-cancer compounds induce DNA damage, including anti-metabolites, platinum agents, topoisomerase inhibitors and alkylating agents. However, their efficacy is limited due to excessive toxicity, resistance and lack of tumour selectivity. Compounds which work in combination with these agents to prevent DNA repair selectively in tumour cells would be extremely beneficial. As the tumour suppressor gene TP53 is commonly mutated in tumour cell lines, the administration of a Wee-1 kinase inhibitor, abrogating the G2 check point, may lead to increased sensitivity to DNA damaging agents. The potential for this has been reported, as silencing of Wee-1 activity was sufficient to sensitize HeLa cells to doxorubicin due to abrogation of G2 arrest. By contrast, in normal breast epithelium due to the fully competent p53 protein, the removal of Wee-1 function had little additional effect compared to doxorubicin alone (Wang et al., 2004, Cancer Biology and Therapy, 3(3), 305-313).

It has been reported that cell lines harbouring mutations in the tumour suppressor gene TP53 had increased sensitivity to DNA damaging agents when co-administered with Wee-1 small molecule inhibitors. Synergistic in vitro and in vivo efficacy has been reported when small molecule inhibitors were combined with gemcitabine, 5-fluorouracil, carboplatin, cisplatin (Hirai et al. 2010, Cancer Biology & Therapy 9:7, 514-522), cytarabine (Tibes et al., 2012, Blood, 119 (12), 2863-2872), Chk-1 inhibitors (Carrasa et al., 2012 Cell Cycle 1:11 (13):2507-2517, Russell et al., 2013 Cancer Res. 15; 73 (2) 776-784) and Src inhibitors (Cozzi et al., 2012, Cell Cycle 11 (5), 1029-1039). Single agent apoptotic efficacy, independent of TP53 status, has been reported in sarcoma cell lines and in patient derived sarcoma samples (Kreahling et al., 2012, Mol. Cancer Ther., 11 (1), 174-182) and efficacy demonstrated in a panel of cancer cell lines in vivo (Guertin et al., 2013 Mol. Cancer Ther. 12 (8) 1442-1452).

Irradiation, via induction of DNA damage, is known to increase phosphorylation of the Tyr15 and Thr14 residues of cdc2, which arrests cells at G2 and allow time for DNA repair, leading to a radio-resistant phenotype. Inhibition of Wee-1 activity by small molecule inhibitors (Wang et al., 2004, Cancer Biology and Therapy 3(3), 305-313), (Caret et al., 2013 Mol. Cancer Ther. 12 (2) 141-150) leads to a reduction in CDC2 phosphorylation abrogation of G2 checkpoint and radiosensitization, with the effect being more pronounced in p53 mutant cell lines.

It has been reported in melanoma that over-expression of Wee-1 is correlated with poor clinical outcome (Magnussen et al, 2012 PLoS One 7; (6) e38254), indicating it may have a significant, role as a biomarker and as a targeted therapy.

Compounds having a kinase inhibitory effect, for example a Wee-1 kinase inhibitory effect, are described in WO 2007/126122, US 2010/0063024, EP 2,213,673, WO 2008/133866, US 2007/0254892, WO 2012/161812, WO 2013/126656, US 2013/0102590, WO 2013/059485 and WO 2013/013031.

WO 2010/067886, WO 2010/067888, US 2011/0135601, EP 2,168,966, WO 2005/090344, US 2009/0048277 and Bioorg. Med. Chem., Lett., 2005, 15, 1931-1935 describe various compounds such as dihydropyrimidopyrimidine, pyridopyrimidinone and pyridopyrimidine derivatives having a kinase inhibitory effect. In particular, the compounds of WO 2005/090344 are said to show activity as protein kinase inhibitors, in particular Src family tyrosine kinase inhibitors. The compounds described in Bioorg. Med. Chem. Lett., 2005, 15, p 1931-1935 are said to be 10-100-fold more potent inhibitors of c-Src than Wee-1, and variation of substituents on the 6-phenyl ring does not markedly alter this preference, 5-Alkyl substituted analogues are said to be generally Wee-1 selective, but at the expense of binding potency.

WO 2013/013031 describes pyridazino[4,5-d]pyrimidin-(6H)-one inhibitors of Wee-1 kinase which are said to be useful for inhibiting kinases such as Wee-1 and in methods of treating diseases such as cancer. Compounds of WO 2013/013031 have a nitrogen atom at the '3-position' of the ring relative to the carbonyl group.

US 2013/0018045 describes various tricyclic-sulfonamide compounds which are useful for inhibiting kinases such as Wee-1 and methods of treating diseases such as cancer.

Compounds of US 2013/0018045 have a sulfonamide group at the '1-position' on the ring and the atoms at the '3- and 4-positions' form part of a fused aryl or heteroaryl ring ("A").

WO 2015/092431 relates to compounds that are useful as inhibitors of the activity of Wee-1 kinase, pharmaceutical compositions comprising these compounds and the use of these compounds in the treatment of cancer.

It is one object of the present invention to overcome at least some of the disadvantages of the prior art or to provide a commercially useful alternative thereto.

It is a further object of the present invention to provide a compound having an enhanced or similar kinase inhibitory effect compared to known compounds or compositions.

It is a further object of the present invention to provide a compound with an improved pCDC2 potency, compared to known compounds or compositions.

It is a further object of the present invention to provide a compound with an improved or comparable kinetic solubility, compared to known compounds or compositions.

It is a further object of the present invention to provide a compound with an improved or comparable permeability, compared to known compounds or compositions.

It is a further object of the present invention to provide a compound with an improved metabolic stability, compared to known compounds or compositions.

It is a further object of the present invention to provide a compound having an enhanced or similar plasma and/or tumor exposure after oral dosing compared to known compounds or compositions.

It is a further object of the present invention to provide a compound having an enhanced or similar bioavailability compared to known compounds or compositions.

It is a further object of the present invention to provide a compound having an enhanced or similar brain penetration compared to known compounds or compositions in order to target brain tumors and metastases.

It is a further object of the present invention to provide a compound having a reduced risk of reactive metabolites compared to known compounds or compositions.

It is a further object of the present invention to provide a compound having a reduced risk of interaction with comedications metabolized by enzymes of the CYP3A family compared to known compounds or compositions.

SUMMARY OF THE INVENTION

In a first aspect the present invention provides a compound of Formula (I):

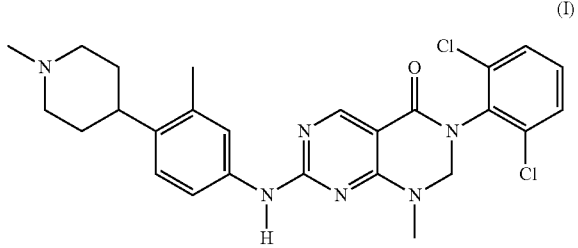 [SMILES: Cc1cc(Nc2ncc3c(n2)N(C)CN(c2c(Cl)cccc2Cl)C3=O)ccc1C1CCN(C)CC1]

(I)

or a pharmaceutically acceptable salt or N-oxide derivative thereof.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a second aspect the present invention provides a pharmaceutical composition comprising the compound of formula (I), or a pharmaceutically acceptable salt or N-oxide derivative thereof, and at least one pharmaceutically acceptable excipient.

In a third aspect the present invention provides the compound of formula (I), or a pharmaceutically acceptable salt or N-oxide derivative thereof, or the pharmaceutical composition as described herein, for use in therapy.

In a fourth aspect the present invention provides the compound of formula (I), or a pharmaceutically acceptable salt or N-oxide derivative thereof, or the pharmaceutical composition as described herein, for use as a medicament.

In a fifth aspect the present invention provides the compound of formula (I), or a pharmaceutically acceptable salt or N-oxide derivative thereof, or the pharmaceutical composition as described herein, for use in treating or preventing cancer.

In a sixth aspect the present invention provides the use of the compound of formula (I), or a pharmaceutically acceptable salt or N-oxide derivative thereof, or the pharmaceutical composition as described herein, for the manufacture of a medicament for treating or preventing cancer.

In an seventh aspect the present invention provides a method of treating or preventing cancer in a human or animal patient comprising administering to a patient in need thereof an effective amount of the compound of formula (I) or a pharmaceutically acceptable salt or N-oxide derivative thereof, or the pharmaceutical composition as described herein.

Other preferred embodiments of the compounds according to the invention appear throughout the specification and in particular in the examples.

The present inventors have surprisingly found that the compound of the present invention displays an improved or similar kinase-inhibitory effect compared to known compounds or compositions. In particular, the compound of the present invention preferably displays an improved or similar Wee-1 kinase-inhibitory effect compared to known compounds or compositions.

The present inventors have surprisingly found that the compound of the present invention displays an improved or similar pCDC2 potency compared to known compounds or compositions.

The present inventors have surprisingly found that the compound of the present invention displays an improved or similar kinetic solubility compared to known compounds or compositions.

The present inventors have surprisingly found that the compound of the present invention displays an improved or similar permeability compared to known compounds or compositions.

The present inventors have surprisingly found that the compound of the present invention displays an improved or similar metabolic stability compared to known compounds or compositions.

The present inventors have surprisingly found that the compound of the present invention displays an enhanced or similar exposure after oral dosing compared to known compounds or compositions.

The present inventors have surprisingly found that the compound of the present invention displays an enhanced or similar bioavailability compared to known compounds or compositions.

The present inventors have surprisingly found that the compound as described herein may exhibit superior physicochemical properties compared with those known in the prior art.

Without wishing to be bound by theory it is thought that the compound of the present invention tends to show the advantageous effects discussed above due to its specific chemical structure.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The compound of the present invention may possess tautomerism. Each tautomeric form is intended to fall within the scope of the invention.

In addition, the compound of the present invention may be provided as a pro-drug. Pro-drugs are transformed, generally in vivo, from one form to the active forms of the drugs described herein. For example, a pro-drug may be formed by protecting the —N—H group with a hydrolysable group that gives —NH on hydrolysis.

In addition, it will be understood that the elements described herein may be the common isotope or an isotope other than the common isotope. For example, one or more hydrogen atom(s) may be $^1H$, $^2H$ (deuterium) or $^3H$ (tritium).

Although the compound of the present invention is present preferably as its free base, either under its anhydrous form or its solvate free form, it may be provided also in the form of its pharmaceutically acceptable salt or as a co-crystal or as a solvate. For example, the compound may be provided having protonated amine groups.

The term "pharmaceutically acceptable salt" refers to an ionic compound formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Preferably, the suitable salt is a hydrochloride or a citrate salt. Further reference is made to the number of literature sources that survey suitable pharmaceutically acceptable salts, for example the Handbook of pharmaceutical salts published by IUPAC.

The present inventors have discovered that the compound of the present invention is useful in the treatment of medical conditions associated with disordered cell growth, including, but not restricted to, cancer, in particular (but not restricted to) cancers associated with inactivation in the tumour suppressor gene TP53. The compound may have utility and activity as a single agent exploiting synthetic or contextual lethality relationships as well as in diseases including cancers with enhanced susceptibility to increased replicative stress and impaired cell cycle progression. Weal inhibitors according to the invention may also be used in combination modalities including combinations with genotoxic agents, radiotherapy, targeted agents and immune-modulators including but not restricted to immune checkpoint inhibitors.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers, and cancers such as adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharangeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

The compound of the present invention is also useful in preparing a medicament that is useful in treating the diseases described above, in particular cancer.

The present invention is further directed to a method of inhibiting Wee-1 activity which comprises administering to a mammal, preferably a human, in need thereof a pharmaceutically effective amount of the compound of the present invention.

The compound of this invention may be administered to mammals, including humans, either alone or, in combination with pharmaceutically acceptable carriers, excipients or diluents, in a pharmaceutical composition, according to standard pharmaceutical practice. The compound can be administered orally or parenterally, including the intravenous, intramuscular, intraperitoneal, subcutaneous, rectal and topical routes of administration.

The present invention also includes within its scope the use of the compound of the present invention in combination with a second or further drug in the treatment of cancer. The second or further drug may be a drug that is already known in the art in the treatment of cancer.

The present invention also includes the use of the compound of the invention in a regime including the step of radiotherapy. The radiotherapy maybe an ordinary method of treatment by x-ray, γ-ray, neutron, α-particle, proton or electron beam irradiation. The co-administration of the compound contained in this invention may lead to the potentiation of the radiation therapy, thus classifying it as a radio-sensitizer.

In particular, cancers often become resistant to therapy. The development of resistance may be delayed or overcome by the administration of a combination of drugs that includes the compound of the present invention, for example in cancers which are known to be resistant to DNA damaging agents, radiotherapy or any other form of treatment agents and modalities.

For example, drugs that may be used in combination with the compound of the present invention may target the same or a similar biological pathway to that targeted by the compound of the present invention or may act on a different or unrelated pathway.

Depending on the disease to be treated, a variety of combination partners may be co-administered with the compounds of the present invention, for example genotoxic agents, targeted agents and immune-modulators. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatirr, antimitotic agents, including vinca alkaloids (vincristine, vinorelbine and vinblastine), taxanes (paclitaxel, docetaxel), epothilones and inhibitors of mitotic kinases including aurora and polo-like kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and pemetrexed; targeted therapies, for example protein kinase inhibitors, including imatinib, gefitinib, sorafenib, sunitinib, erlotinib, dasatinib, and lapatinib; proteasome inhibitors, including bortezomib; histone deacetylase inhibitors, including valproate and SAHA; cell cycle and checkpoint inhibitors, including CDK4/6, CDC7, CHK1 and CHK2; DNA-repair-modulators, including but not restricted to inhibitors of PARP, DNA-PK, ATM, ATR; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumornab tiuxetan; hormonal therapies, including antiestrogens (tamoxifen, raloxifen, anastrazole, letrozole, exemestane) antiandrogens (flutamide, bicalutamide), Luteinising Hormone analogues or antagonists, peptide receptor radionuclide therapies, including luthatera, immunotheries, including anti-PD1 or antiPDL1, and IDO inhibitors.

With regard to combination therapy the compound of the present invention may be administered separately, sequentially, simultaneously, concurrently or may be chronologically staggered with one or more standard therapeutics such as any of those mentioned above.

The present invention provides a compound of Formula (I):

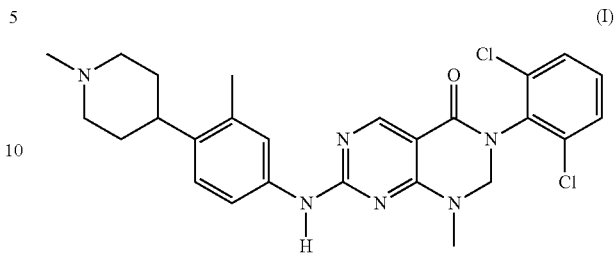

or a pharmaceutically acceptable salt or N-oxide derivative thereof.

Preferably, there is provided the compound of formula (I), or a pharmaceutically acceptable salt or N-oxide derivative thereof, and at least one pharmaceutically acceptable excipient.

Suitable pharmaceutically acceptable excipients would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

Preferably, there is provided a pharmaceutical composition comprising the compound of formula (I), or a pharmaceutically acceptable salt or N-oxide derivative thereof, and at least one pharmaceutically acceptable excipient.

Preferably, there is provided a pharmaceutical composition comprising the compound of formula (I), or a pharmaceutically acceptable salt or N-oxide derivative thereof, comprising one or more further pharmaceutically active agents. Preferably, in certain embodiments, the pharmaceutical composition further comprises an anti-cancer agent, for example as a combination therapy as described herein. In such embodiments, a suitable anti-cancer agent may be any one or more of a genotoxic agent, a targeted agent and an immune-modulator.

Preferably, there is provided the compound of Formula (I), or a pharmaceutically acceptable salt or N-oxide derivative thereof, or the pharmaceutical composition as described herein, for use in therapy.

Preferably, there is provided the compound of Formula (I), or a pharmaceutically acceptable salt or N-oxide derivative thereof, or the pharmaceutical composition as described herein, for use as a medicament.

Preferably, there is provided the compound of Formula (I), or a pharmaceutically acceptable salt or N-oxide derivative thereof, or the pharmaceutical composition as described herein, for use in treating or preventing cancer. Preferably the cancer is selected from colon and rectal (colorectal)

cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, there is provided the use of the compound of Formula (I), or a pharmaceutically acceptable salt or N-oxide derivative thereof, or the pharmaceutical composition as described herein, for the manufacture of a medicament for treating or preventing cancer. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, there is provided a method of treating or preventing cancer in a human or animal patient comprising administering to a patient in need thereof an effective amount of a compound of Formula (I), or a pharmaceutically acceptable salt or N-oxide derivative thereof, or the pharmaceutical composition as described herein. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, the compound of the present invention has an $IC_{50}$ value for Wee-1 kinase of about 0.1 nM to about 1 nM. The method for determining the $IC_{50}$ value of a compound for Wee-1 kinase is described in WO 2015/092431 (see page 350 to 351).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

Experimental Section

Abbreviations aq; aqueous; dba: dibenzylideneacetone; SCM; dichloromethane; DIPEA: diisopropylethylamine (Hunig's base); DMF: N,N-dimethylformamide; DMF: N,N-dimethylformamide dimethyl acetal; dppf: 1,1'-bis(diphenylphosphino)ferrocene; EtOAc: ethyl acetate: ESI; electrospray ionisation; h: hour; HPLC: high pressure liquid chromatography; LC: liquid chromatography; LCMS: liquid chromatography mass spectrometry; M: molar; m/z: mass-to-charge ratio; mCPBA: 3-chloroperbenzoic acid; MeOH: methanol; min: minutes; MS: mass spectrometry; NMR: nuclear magnetic resonance; $R_T$: retention time; RB: round-bottomed; RT: room temperature; SOP: standard operating procedure; SM: starting material; TFA: trifluoroacetic acid; THF: tetrahydrofuran; TLC: thin layer chromatography.

General Experimental Conditions

Solvents and Reagents

Common organic solvents that were used in reactions (e.g. THF, DMF, DCM, IPA, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Flash Chromatography

Purification of compounds by flash chromatography was achieved using a Biotage Isolera Four system. Unless otherwise stated, Biotage KP-Sil SNAP cartridge columns (10-340 g) were used along with the stated solvent system and an appropriate solvent gradient depending on compound polarity (determined by TLC analysis). In the case of more polar and basic compounds, Biotage KP-NH SNAP cartridge columns (11 g) were used.

NMR Spectroscopy $^1$H NMR spectra were recorded at ambient temperature using a Bruker Avance (500 MHz) spectrometer or a Balker Avance (400 MHz) spectrometer. All chemical shifts ($\delta$) are expressed in ppm. Residual solvent signals were used as an internal standard and the characteristic solvent peaks were corrected to the reference data outlined in *J. Org. Chem.*, 1997. 62, p 7512-7515; in other cases, NMR solvents contained tetramethylsilane, which was used as an internal standard.

High Pressure Liquid Chromatography

Liquid Chromatography Mass Spectrometry (LCMS) experiments to determine retention times (RT) and associated mass ions were performed using one of the following methods:

Method A: The system consists of an Agilent Technologies 6140 single quadrupole mass spectrometer linked to an Agilent Technologies 1290 Infinity LC system with UV diode array detector and autosampler. The spectrometer consists of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD 1.8 micron 50×2.1 mm maintained at 40° C. Mobile phases: A) 0.1% (v/v) formic acid in water; B) 0.1% (v/v formic acid in acetonitrile.

| Gradient Time (min) | How (mL/min) | % A | % B |
| --- | --- | --- | --- |
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method B: The system consists of an Agilent Technologies 6130 quadrupole mass spectrometer linked to an Agilent Technologies 1290 Infinity LC system with UV diode array detector and autosampler. The spectrometer consists of an electrospray ionization source operating in positive and negative ion mode. LCMS experiments were performed on each sample submitted using the following conditions: LC Column: Agilent Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | How (mL/min) | % A | % B |
|---|---|---|---|
| 0.00 | 1.0 | 80 | 20 |
| 1.80 | 1.0 | 0 | 100 |
| 2.20 | 1.0 | 0 | 100 |
| 2.50 | 1.0 | 80 | 20 |
| 3.00 | 1.0 | 80 | 20 |

Intermediate 1: tert-butyl 4-(4-amino-2-methylphenyl)piperidine-1-carboxylate

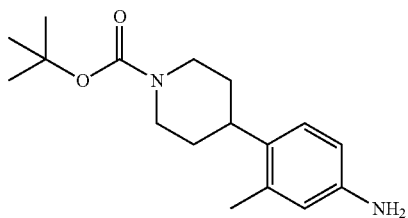 [SMILES: Cc1cc(N)ccc1C1CCN(C(=O)OC(C)(C)C)CC1]

Step 1: tert-Butyl 4-(2-methyl-4-nitrophenyl)-5,6-dihydropyridine-1 (2H)-carboxylate 1-Bromo-2-methyl-4-nitrobenzene (123 g, 0.572 mol) and N-tert-butyl 4-(4,4,5,5-tetramethyl-1,3,2-dioxaborolan-2-yl)-5,6-dihydropyridine-1(2H)-carboxylate (177 g, 0.571 mmol) were dissolved in 1,4-dioxane (2.5 L). 3M Sodium carbonate solution (570 mL, 1.71 mol) was added, the mixture was degassed and placed under a nitrogen atmosphere. PdCl$_2$(dppf) dichloromethane adduct (9.3 g, 0.011 mol) was added and the mixture was heated at 100° C. overnight. The mixture was diluted with water and extracted with ethyl acetate (three times 1 L). The combined organic extracts were washed with brine, dried over MgSO$_4$, filtered and concentrated in vacuo. The residue was purified by flash chromatography (0-50% EtOAc/hex) to give 154 g (94.5%) of the title compound as yellowish crystals.

Step 2: tert-butyl 4-(4-amino-2-methylphenyl)piperidine-1-carboxylate tert-Butyl 4-(2-methyl-4-nitrophenyl)-5,6-dihydropyridine-1(2H)-carboxylate (130 g, 0.408 mol) was dissolved in methanol (3.5 L) using a 5 L Parr reaction bottle. After the degassing the mixture, Pd/C (10%) (13 g) was added and the suspension was shaken under 55 psi hydrogen pressure overnight at RT. The mixture was filtered through a pad of Celite™ and the filtrate was concentrated under reduced pressure to provide 117 g (981%) of the title compound as a light beige solid.

The analytical data is in accordance with Example 37 step 4 as described in US2007/0254892A1.

EXAMPLES

The following non-limiting example further illustrates the present invention.

Example 1: 3-(2,6-dichlorophenyl)-1-methyl-7-((3-methyl-4-(1-methylpiperidin-4-yl)phenyl)amino)-2,3-dihydropyrimido[4,5-d]pyrimidin-4(1H)-one

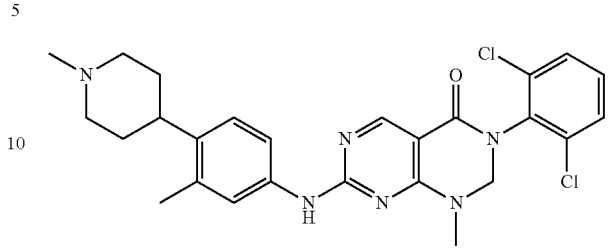

Step 1: 4-chloro-N-(2,6-dichlorophenyl)-2-(methylthio)pyrimidine-5-carboxamide

To a solution of 2,6-dichloroaniline (41.02 g, 253 mmol) and pyridine (25.03 g, 316 mmol) in CH$_2$Cl$_2$ (400 mL) a solution of 4-chloro-2-(methylthio)pyrimidine-5-carbonyl chloride (56.5 g, 253 mmol) in CH$_2$Cl$_2$ (400 mL) was added dropwise at 0° C. The reaction mixture was stirred at RT for 2 days, the solvent was evaporated in vacuo and the remaining residue was washed with water twice, followed by 10% sq. HCl and water. The crude product was purified by recrystallization from EtOH to give 67.7 g (76.7%) of the title compound as a white solid. LCMS (Method B): $R_T$=1.53 min, m/z=348/350 [M+H]$^+$.

Step 2: N-(2,6-dichlorophenyl)-4-(methylamino)-2-(methylthio)pyrimidine-5-carboxamide To a solution of 4-chloro-N-(2,6-dichlorophenyl)-2-(methylthio)pyrimidine-5-carboxamide (70 g, 201 mmol) in THF (1 L) a solution of MeNH$_2$ (40% in water, 46.74 g, 603 mmol) was added at 0° C. The resulting reaction mixture was stirred at room temperature overnight and the solvent was evaporated in vacuo. The remaining residue washed with water twice and dried to yield 68.35 g (99%) of the title compound as a white solid. LCMS (Method A): $R_T$=1.21 min, m/z=343/345 [M+H]$^+$.

Step 3: 3-(2,6-dichlorophenyl)-1-methyl-7-(methylthio)-2,3-dihydropyrimido[4,5-d]pyrimidin-4(1H)-one N-(2,6-Dichlorophenyl)-4-(methylamino)-2-(methylthio)pyrimidine-5-carboxamide (131 g, 382 mmol) was suspended in anhydrous acetonitrile (1.5 L), using a 5 L RB flask, and cesium carbonate (203.3 g, 1190 mmol) was added, followed by dibromomethane (132.7 g, 763 mmol). The mixture was heated to 80° C. while stirring for 7 days and the resulting mixture was filtered. The residue was washed with two portions of hot acetonitrile (200 mL) and the combined filtrates were concentrated in vacuo. The crude product was purified by crystallization from MeCN to yield 59.6 g (44%) of the title compound as a pale yellow solid. LCMS (Method A): $R_T$=1.26 min, m/z=355/357 [M+H]$^+$.

Step 4: tert-butyl 4-(4-((6-(2,6-dichlorophenyl)-8-methyl-5-oxo-5,6,7,8-tetrahydropyrimido[4,5-d]pyrimidin-2-yl)amino)-2-methylphenyl)piperidine-1-carboxylate To 6-(2,6-dichlorophenyl)-8-methyl-2-methylsulfanyl-7H-pyrimido[4,5-d]pyrimidin-5-one (10.0 g, 28 mmol) in DCM (440 mL) was charged, a solution of 3-chloroperoxybenzoic acid (7.63 g, 31 mmol) in DCM (75 mL) at RT and the reaction was stirred for two hours. To the reaction mixture was added eq. Na$_2$S$_2$O$_3$ and the layers were separated using a phase separator. The organic layer was concentrated to dryness and tert-butyl 4-(4-amino-2-methylphenyl)piperidine-1-carboxylate (8.17 g, 28 mmol) and 2-propanol (625 mL) were added to the residue. The reaction, was then heated at 95° C. overnight. The reaction was concentrated and the residue purified by flash chromatography (Biotage 340 g KP-Sil; 10-45% EtOAc in cyclohexane) to the title compound (11.13 g, 66%) as a white solid. LCMS (Method A): R$_T$ 1.86 min, m/z=597/599 [M+H]$^+$ Step 5: 3-(2,6-dichlorophenyl)-1-methyl-7-((3-methyl-4-(piperidin-4-yl)phenyl)amino)-2,3-dihydropyrimido[4,5-d]pyrimidin-4(1H)-one hydrochloride tert-butyl 4-[4-[[6-(2,6-dichlorophenyl)-8-methyl-5-oxo-7H-pyrimido[4,5-d]pyrimidin-2-yl]amino]-2-methyl-phenyl]piperidine-1-carboxylate (7.0 g, 11.7 mmol) was dissolved in DCM (300 mL) and 4N HCl in dioxane (35 mL, 140 mmol) was added and the mixture was stirred overnight at RT. The solid was collected by filtration through a sintered funnel and washed with DCM and dried on the sinter to afford the title compound (6.3 g, quant. yield). LCMS (Method A): R$_T$ 0.80 min, m/z=497/499 [M+H]$^+$ Step 6: 3-(2,6-dichlorophenyl)-1-methyl-7-((3-methyl-4-(1-methylpiperidin-4-yl)phenyl)amino)-2,3-dihydropyrimido[4,5-d]pyrimidin-4(1H)-one To a suspension of 6-(2,6-dichlorophenyl)-8-methyl-2-[3-methyl-4-(4-piperidyl)anilino]-7H-pyrimido[4,5-d]pyrimidin-5-one hydrochloride (6.77 g, 12.7 mmol) in acetonitrile (90 mL) was added methanol (20 mL) and 37% aqueous formaldehyde solution (12.76 mL, 63.4 mmol). The resulting solution was cooled to 0° C. and sodium triacetoxyborohydride (13.44 g, 63.4 mmol) was added portion wise. The reaction was stirred at 0° C. for 1 hr and subsequently the solvent was concentrated in vacuo. The residue was taken up in DCM and washed with 2M aq.Na$_2$CO$_3$, water and brine after which the biphasic mixture was passed through a phase separator and the resulting organic phase was concentrated to obtain a solid. Recrystallisation from ethyl acetate afforded the title compound (3.83 g, 59%) as a white solid. LCMS (Method A): R$_T$ 0.70 min, m/z=511/513 [M+H]$^+$, $^1$H NMR (500 MHz, DMSO-d$_6$): δ 9.75 (br s, 1H), 8.47 (s, 1H), 7.65 (d, 2H), 7.52-7.62 (m, 2H), 7.46-7.51 (m, 1H), 7.14 (d, 1H), 4.98 (s, 2H), 3.12 (s, 3H), 2.79-2.91 (m, 2H), 2.55-2.62 (m, 1H), 2.28 (s, 3H), 2.20 (s, 3H), 1.93-2.03 (m, 2H), 1.58-1.68 (m, 4H).

Comparative Example 1: 3-(2-chloro-6-methylphenyl)-1-methyl-7-((3-methyl-4-(1-methylpiperidin-4-yl)phenyl)amino)-2,3-dihydropyrimido[4,5-d]pyrimidin-4(1H)-one Step 1: 4-chloro-N-(2-chloro-6-methylphenyl)-2-methylthio)pyrimidine-5-carboxamide 2-chloro-6-methylaniline (14 g, 62.8 mmol) was converted according to example 1 step 1 to result in the title compound (10 g; 30.5 mmol, 48%) as a white solid. LCMS (Method A): R$_T$=1.28 min, m/z=328/330 [M+H]$^+$.

Step 2: N-(2-chloro-6-methylphenyl)-4-(methylamino)-2-(methylthio)pyrimidine-5-carboxamide 4-Chloro-N-(2-chloro-6-methylphenyl)-2-(methylthio)pyrimidine-5-carboxamide (7 g, 21.33 mmol) was converted according to example 1 step 2 to result in the title compound (6 g; 18.59 mmol, 87%) as an off-white solid, LCMS (Method A): R$_T$=1.22 min, m/z=323/325 [M+H]$^+$. The analytical data is in accordance with Example 92, step 1 as described in WO2015/092431.

Step 3: 3-(2-chloro-6-methylphenyl)-1-methyl-7-(methylthio)-2,3-dihydropyrimido[4,5-d]pyrimidin-4(1H)-one N-(2-chloro-6-methylphenyl)-4-(methylamino)-2-(methylthio)pyrimidine-5-carboxamide (6 g, 18.59 mmol) was converted according to example 1 step 2 to result in the title compound (2.9 g; 8.66 mmol, 47%) as an off-white solid. LCMS (Method A): R$_T$=1.25 min, m/z=335/337 [M+H]$^+$. The analytical data is in accordance with Example 92, step 2 as described in WO2015/092431.

Step 4: tert-butyl 4-(4-((6-(2-chloro-6-methylphenyl)-8-methyl-5-oxo-5,6,7,8-tetrahydropyrimido[4,5-d]pyrimidin-2-yl)amino)-2-methylphenyl)piperidine-1-carboxylate 3-(2-chloro-6-methylphenyl)-1-methyl-7-(methylthio)-2,3-dihydropyrimido[4,5-d]pyrimidin-4(1H)-one (150 mg, 0.45 mmol) was dissolved in DCM (6 mL) and mCPBA (121 mg, 0.49 mmol) was added. The reaction mixture was stirred for 30 min, at RT. The reaction mixture was diluted with DOM to 10 mL and washed with aq. thiosulfate solution. The organic layer was separated, dried (anh. MgSO$_4$) and the solvent was evaporated under reduced pressure. The residue was suspended in 2-propanol (6 mL) and tert-butyl 4-(4-amino-2-methylphenyl)piperidine-1-carboxylate (130 mg, 0.45 mmol) was added. The reaction mixture was stirred at 90° C. overnight. The volatiles were evaporated and the product was purified by flash chromatography (20-80% EtOAc in cyclohexane) yielding the title compound as a clear oil (206 mg, 80%). LCMS (Method B): R$_T$=1.80 min, m/z=577 [M+H]$^+$.

Step 5: 3-(2-chloro-6-methylphenyl)-1-methyl-7-((3-methyl-4-(piperidin-4-yl)phenyl)amino)-2,3-dihydropyrimido[4,5-d]pyrimidin-4(1H)-one hydrochloride tert-Butyl 4-[4-[[6-(2-chloro-6-methyl-phenyl)-8-methyl-5-oxo-7H-pyrimido[4,5-d]pyrimidin-2-yl]amino]-2-methylphenyl]piperidine-1-carboxylate (206 mg, 0.36 mmol) was dissolved in DCM (4 mL) and TFA (2 mL) was added. The reaction mixture was stirred for 30 min at RT. The volatiles were evaporated under reduced pressure and the residue was dissolved in DCM (2 mL) and loaded onto an SCX-2-cartridge (5 g; column eluted with DCM prior to use). The cartridge was washed with 20% MeOH in DCM and the

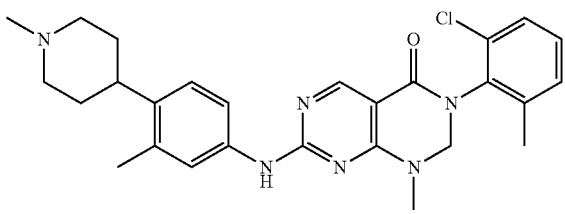 [SMILES: Cc1cc(Nc2ncc3c(n2)N(C)CN(c2c(C)cccc2Cl)C3=O)ccc1C1CCN(C)CC1]

desired compound was eluted with 20% 7N NH₃ MeOH in DCM. The product containing fractions were evaporated under reduced pressure yielding the title compound as a white solid (138 mg, 81%). LCMS (Method A): $R_T$=0.80 min, m/z=477 [M+H]⁺.

Step 6: 3-(2-chloro-6-methylphenyl)-1-methyl-7-((3-methyl-4-(1-methylpiperidin-4-yl)phenyl)amino)-2,3-dihydropyrimido[4,5-d]pyrimidin-4(1H)-one 6-(2-chloro-6-methyl-phenyl)-8-methyl-2-[3-methyl-4-(4-piperidyl)anilino]-7H-pyrimido[4,5-d]pyrimidin-5-one (70 mg, 0.15 mmol) was dissolved in MeCN (3 mL)/MeOH (1 mL) mixture and 37% aqueous formaldehyde solution (0.11 mL, 1.47 mmol) was added followed by sodium triacetoxy borohydride (311 mg, 1.47 mmol). The reaction mixture was stirred at RT overnight. The volatiles were evaporated under reduced pressure and the residue was dissolved in DCM/1M NaOH (5 mL/5 mL). The organic layer was separated and the aqueous phase was extracted with DCM (2×5 mL). The organic extracts were combined, dried (anh. $K_2CO_3$) and evaporated under reduced pressure. The product was lyophilised (MeOH/MeCN/water) yielding the title compound as a white solid (58 mg, 80%). LCMS (Method B): $R_T$=0.79 min, m/z=491 [M+H]⁺, ¹H NMR (500 MHz, DMSO-$d_6$) δ 9.70 (s, 1H), 8.45 (s, 1H), 7.63-7.52 (m, 2H), 7.48-7.41 (m, 1H), 7.38-7.28 (m, 2H), 7.13 (d, 1H), 4.98-4.86 (m, 2H), 3.11 (s, 3H), 2.87 (d, 2H), 2.62-2.53 (m, 1H), 2.27 (s, 3H), 216 (s, 3H), 2.19 (s, 3H), 2.03-1.92 (m, 2H), 1.70-1.56 (m, 4H).

Comparison of the Compound of the Present Invention with Prior Art Compounds and Other Compounds:

Compound as described in Example 1 was tested for Wee-1 kinase inhibitory effect (Wee-1 $IC_{50}$ value), Wee-1 potency in cells (pCDC2 value), kinetic solubility, permeability in caco-2 cells (Cato-2 $P_{app}$ value), in vivo plasma clearance (CL value) and elimination half-life ($T_{1/2}$ value) in rat after intravenous administration, plasma exposure in rat after oral administration (AUC value), oral bioavailability in rat (F % value), brain plasma concentration ratio in healthy mouse, tumor:plasma concentration ratio in tumor-bearing mouse, in-vivo CYP3A4/5 time-dependant inhibition (CYP3A4/5 $IC_{50}$ shift value) and detection of reactive metabolites in human hepatocytes, Comparative compounds were also tested using the same tests. The test methods employed to determine Wee-1 kinase inhibitory effect, Wee-1 potency in cells and kinetic solubility were the same as those taught in WO 2015/092431 (see page 350 to 358). The other test methods employed were as follows:

i. Determination of Caco-2 permeability at pH 6.5 (pH7.4 for Comparative Example 6) was carried out at Cyprotex Ltd using standard protocols and SOPs.

ii. Determination of pharmacokinetic parameters (CL/$T_{1/2}$/AUC1F %) in male Sprague-Dawley rats on Example 1 and Comparative Examples 6 and 165 was carried out at Axis BioServices Ltd using standard protocols and SOPs. Dosing was as follows: single oral dose 5 mg/kg; single intravenous dose 1 mg/kg.

iii. Determination of pharmacokinetic parameters (CUT$_{1/2}$/AUC/F %) in male Sprague-Dawley rats on Comparative Example 18 was carried out at BioDuro using standard protocols and SOPs. Dosing was as follows: oral dosing 5 mg/kg; intravenous dosing 1 mg/kg iv. Determination of brain:plasma concentration ratio in the healthy mouse was carried out at Bioduro Inc. (Example 1) and at Axis Bioservices Ltd (Comparative Example 18) using standard protocols and SOPs. Dosing was as follows: repeated oral dose of 30 mg/kg, once a day for 7 days. Concentrations were measured at 4 h post dose on day 7.

v. Determination of tumor:plasma concentration ratio in the tumor-bearing mouse was carried out at Axis Bioservices Ltd using standard protocols and SOPs. Dosing was as follows: single oral dose of 30 mg/kg.

vi. Determination of CYP3A4/5 time-dependent inhibition (CYP3A4/5 $IC_{50}$ shift value) was carried out at Cyprotex Ltd using standard protocols and SOPs. The in-vitro test system was: pooled human liver microsomes; a 30-min preincubation step with and without NADPH was included to observe the $IC_{50}$ shift.

vii. Determination of the formation of reactive metabolites was carried out at Admescope Ltd using standard protocols and SOPs. The in-vitro test system was: human hepatocytes; the duration of incubation was: 2 hours; the technique for metabolite analysis was: LC-MS/MS.

The compound described in Example 1 presents an improved chemical stability in solution (Buffer at pH 7.4 and in DMSO). It also shows an improved solubility in a fasted state simulated gastric fluid (FaSSGF).

The data is provided in Table 1a and 1b below:

TABLE 1a

Comparison of Examples 6, 18, 95, 165, 178 and 183 of WO 2015/092431, and Comparative Example 1, with Example 1 of the present invention

| Structure | Example Number | Wee1 $IC_{50}$ [nM] | pCDC2 $EC_{50}$ [nM] | Kinetic solubility [µM] | caco-2 $P_{app}$ [10⁶ cm/s] A-B pH 6.5 | Rat PK CL (mL/ min/ kg) | Rat PK $AUC_{inf}$ (h · ng/ mL) | F % |
|---|---|---|---|---|---|---|---|---|
| (structure shown) | 1 | 0.8 | 188 | 215 | 8.9 | 14 | 1324 | 35 |

TABLE 1a-continued

Comparison of Examples 6, 18, 95, 165, 178 and 183 of WO 2015/092431, and Comparative Example 1, with Example 1 of the present invention

| Structure | Example Number | Wee1 IC$_{50}$ [nM] | pCDC2 EC$_{50}$ [nM] | Kinetic solubility [μM] | caco-2 P$_{app}$ [10$^6$ cm/s] A-B pH 6.5 | Rat PK CL (mL/min/kg) | AUC$_{inf}$ (h · ng/mL) | F % |
|---|---|---|---|---|---|---|---|---|
| | CE 6 | 2.7 | 223 | 170 | 6.6 (pH 7.4) | 26 | 1363 | 41 |
| | CE 18* | 3.7 | 223 | 200 | 0.3 | 48 | 120 | 7 |
| | CE 95* | 7.9 | 378 | 123 | n.d. | n.d. | n.d. | n.d. |
| | CE 165* | 3.1 | 347 | 194 | 0.3 | 27 | 397 | 8 |
| | CE 178* | 3.2 | 371 | 55 | 8.1 | n.d. | n.d. | n.d. |
| | CE 183* | 3.1 | 502 | 60 | n.d. | n.d. | n.d. | n.d. |

TABLE 1a-continued

Comparison of Examples 6, 18, 95, 165, 178 and 183 of WO 2015/092431, and Comparative Example 1, with Example 1 of the present invention

| | | | | | caco-2 | Rat PK | | |
|---|---|---|---|---|---|---|---|---|
| Structure | Example Number | Wee1 $IC_{50}$ [nM] | pCDC2 $EC_{50}$ [nM] | Kinetic solubility [μM] | $P_{app}$ [$10^6$ cm/s] A-B pH 6.5 | CL (mL/ min/ kg) | $AUC_{inf}$ (h · ng/ mL) | F % |
| [structure] | CE 1 | 2.8 | 695 | 189 | n.d. | n.d. | n.d. | n.d. |

*Example Number in WO 2015/092431;
n.d. = not determined;
CE = Comparative Example.

TABLE 1b

Comparison of Examples 6 and 165 of WO 2005/092431 with Example 1 of the present invention

| | | | | Rat | Mouse tissue distribution | |
|---|---|---|---|---|---|---|
| Structure | Example Number | CYP3A4/5 $IC_{50}$ shift | Reactive metabolite detected | PK $T_{1/2}$ (h) | brain/ plasma ratio | tumor/ plasma ratio |
| [structure] | 1 | 1.0–1.8 | no | 4.5 | 0.69 | 4.0 (±1.04) |
| [structure] | CE 6* | 2.3–3.0 | yes | 3.7 | 0.16 | 5.7 (±2.81) |
| [structure] | CE 165* | n.d. | n.d. | 2.1 | n.d. | n.d. |

*Example Number in WO 2015/092431;
n.d. = not determined;
CE = Comparative Example.

Table 1a shows that the compound of the present invention displays an enhanced Wee-1 kinase inhibitory effect, an enhanced Wee-1 potency in cells, an enhanced or similar kinetic solubility, an enhanced or similar permeability, an enhanced in vivo metabolic stability in rat, enhanced exposure in rat and/or enhanced bioavailability in rat, compared to Examples 18, 95, 165, 178 and 183 of WO 2015/092431, and Comparative Example 1.

The invention claimed is:

1. A compound having the formula (I):

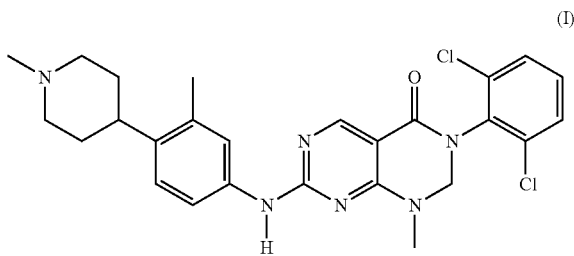 [SMILES: Cc1cc(Nc2ncc3c(n2)N(C)CN(c2c(Cl)cccc2Cl)C3=O)ccc1C1CCN(C)CC1]

or a pharmaceutically acceptable salt or N-oxide derivative thereof.

2. The compound of claim 1, or a pharmaceutically acceptable salt or N-oxide derivative thereof, and at least one pharmaceutically acceptable excipient.

3. A pharmaceutical composition comprising the compound of claim 1, or a pharmaceutically acceptable salt or N-oxide derivative thereof, and at least one pharmaceutically acceptable excipient.

4. The pharmaceutical composition of claim 3 comprising one or more further pharmaceutically active agents.

5. A method of treating cancer in a human or animal patient comprising administering to a patient in need thereof an effective amount of a compound according to claim 1, or a pharmaceutically acceptable salt or N-oxide derivative thereof, wherein the cancer is selected from the group consisting of colorectal, pancreatic, cervical, ovarian, breast, and non-small cell lung cancers.

6. A method of treating cancer in a human or animal patient comprising administering to a patient in need thereof an effective amount of the pharmaceutical composition according to claim 3, wherein the cancer is selected from the group consisting of colorectal, pancreatic, cervical, ovarian, breast, and non-small cell lung cancers.

7. The method of claim 5, wherein the cancer is colorectal cancer.

8. The method of claim 5, wherein the cancer is non-small cell lung cancer.

9. The method of claim 5, wherein the cancer is ovarian cancer.

10. The method of claim 6, wherein the cancer is colorectal cancer.

11. The method of claim 6, wherein the cancer is non-small cell lung cancer.

12. The method of claim 6, wherein the cancer is ovarian cancer.

* * * * *